(12) United States Patent
Abe et al.

(10) Patent No.: US 7,700,330 B2
(45) Date of Patent: *Apr. 20, 2010

(54) METHOD OF PURIFYING AMIDE COMPOUND

(75) Inventors: Takeya Abe, Chiba (JP); Kiyoshi Itou, Chiba (JP); Kenju Sasaki, Chiba (JP); Seiichi Watanabe, Chiba (JP); Tamotsu Asano, Chiba (JP)

(73) Assignee: Mitsui Chemicals, Inc., Minato-Ku, Tokyo (JP)

( * ) Notice: Subject to any disclaimer, the term of this patent is extended or adjusted under 35 U.S.C. 154(b) by 959 days.

This patent is subject to a terminal disclaimer.

(21) Appl. No.: 09/936,514

(22) PCT Filed: Jan. 12, 2001

(86) PCT No.: PCT/JP01/00313

§ 371 (c)(1),
(2), (4) Date: Sep. 14, 2001

(87) PCT Pub. No.: WO01/53253

PCT Pub. Date: Jul. 26, 2001

(65) Prior Publication Data
US 2003/0104586 A1    Jun. 5, 2003

(30) Foreign Application Priority Data
Jan. 17, 2000  (JP) ............................. 2000-007993

(51) Int. Cl.
C12P 13/02 (2006.01)
C12N 9/88 (2006.01)
C12N 1/20 (2006.01)
C12N 1/00 (2006.01)
C07H 21/04 (2006.01)
C07C 233/00 (2006.01)

(52) U.S. Cl. ................. 435/129; 435/232; 435/252.3; 435/254.11; 536/23.2; 564/123

(58) Field of Classification Search ................. 435/129, 435/232, 252.3, 254.11, 254.1; 536/23.2; 564/123
See application file for complete search history.

(56) References Cited

U.S. PATENT DOCUMENTS

| 3,923,741 A | 12/1975 | Asano et al. | |
| 5,910,432 A * | 6/1999 | Ito et al. | ..................... 435/129 |
| 6,043,061 A | 3/2000 | Ishii et al. | |
| 6,849,432 B2 * | 2/2005 | Abe et al. | ..................... 435/129 |

FOREIGN PATENT DOCUMENTS

| CN | 1218834 A | 6/1999 |
| CN | 1224711 A | 8/1999 |
| EP | 0182578 | 5/1986 |
| EP | 0188068 | 7/1986 |
| JP | 50-83323 A | 7/1975 |
| JP | 52-35648 | 9/1977 |
| JP | 61-115058 | 6/1986 |
| JP | 61-115495 | 6/1986 |
| JP | 11 089 575 | 4/1999 |
| WO | WO 99/55719 | * 11/1999 |

OTHER PUBLICATIONS

Chen. J Biol Chem. Jan. 25, 1967;242(2):173-81.*
Rezende et al. J Gen Appl Microbiol. Aug. 1999;45(4):185-192.*
Li Ying Xiu et al., "Purification of acrylamide in aqueous solution by activated carbon" XP002936711 Chemical Abstracts, vol. 127, 1997, Columbus, Ohio, US; abstract No. 346682.

* cited by examiner

*Primary Examiner*—Christian L Fronda
(74) *Attorney, Agent, or Firm*—Buchanan Ingersoll & Rooney PC

(57) ABSTRACT

The invention is to provide a process for effectively removing impurities contained in an amide compound-containing solution by making an amide compound-containing solution, particularly an amide compound-containing solution produced by a hydration reaction of a nitrile compound by using a microorganism fungus body containing nitrile hydratase or a processed product of the microorganism fungus body, in contact with activated carbon under acidic conditions.

15 Claims, No Drawings

SEQUENCE LISTING

<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
<223> OTHER INFORMATION: primer

<400> SEQUENCE: 1
aacatcatgc gcaagtcg                                                 18

<210> SEQ ID NO 2
<211> LENGTH: 17
<212> TYPE: DNA
<213> ORGANISM: Artificial Sequence

```
<220> FEATURE:
<223> OTHER INFORMATION: primer

<400> SEQUENCE: 2
caggaaacag ctatgac                                              17

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
ggccagtgcc tagcttacat                                           20

<210> SEQ ID NO 4
<211> LENGTH: 17
<212> TYPE: DNA
<213> ORGANISM: Artificial Sequence
<220> FEATURE:
<223> OTHER INFORMATION: primer

<400> SEQUENCE: 4
gttttcccag tcacgac                                              17

<210> SEQ ID NO 5
<211> LENGTH: 18
<212> TYPE: DNA
<213> ORGANISM: Artificial Sequence
<220> FEATURE:
<223> OTHER INFORMATION: primer

<400> SEQUENCE: 5
aactggtaca aggagccg                                             18

<210> SEQ ID NO 6
<211> LENGTH: 18
<212> TYPE: DNA
<213> ORGANISM: Artificial Sequence
<220> FEATURE:
<223> OTHER INFORMATION: primer

<400> SEQUENCE: 6
ccgaactaca gcgtctac                                             18
```

METHOD OF PURIFYING AMIDE COMPOUND

This application is a 371 National Stage filing of PCT application No. PCT/JP01/00313, filed Jan. 12, 2001; which claims foreign priority under 35 § U.S.C. 119(a)-(d) to foreign patent application 2000-7933, filed in Japan on Jan. 17, 2000.

TECHNICAL FIELD

The present invention relates to a purification process of an amide compound. More particularly, it relates to a process for effectively obtaining an amide compound having high purity by treating a liquid containing an amide compound with activated carbon

BACKGROUND OF THE INVENTION

In a production liquid of an amide compound, particularly an amide compound obtained by hydration of a nitrile compound, impurities, such as a polymeric compound, a surfactant, a coloring component, an eluted component and the like, are generally present while the species thereof are different depending on the production process thereof. In order to remove them, for example, a purification process using activated carbon is described in JP-A-61-115495 and JP-A-61-122253 (EP-A-182578), a purification process using an ion exchange membrane is disclosed in JP-A-61-115058, and a purification process by a porous hollow fiber film is disclosed in JP-A-61-122227 (EP-A-188068).

However, the purification processes using an ion exchange membrane and a porous hollow fiber film cannot avoid economical demerits upon practice, such as necessity of a special purification equipment and the like.

In the purification process using activated carbon, while no special equipment is required, impurities are still present in the resulting product, and the process is insufficient from the standpoint of efficiency. Particularly, in the case where an amide compound is produced by directly hydrating a nitrile compound by using a nitrile hydratase, which is an enzyme having an ability of hydrating a nitrile, or the like, protein originated from microorganisms mixed in the reaction solution is insufficiently removed by the purification process by activated carbon according to the conventional technique, and as a result, the reaction solution is liable to be foamed when it is a trace amount, or the reaction solution becomes clouded when the amount is large, whereby the quality of the product is adversely affected.

Therefore, an object of the invention is to provide a process for effectively removing impurities contained in a solution containing an amide compound. More specifically, an object of the invention is to provide a simple and effective purification process in the case where an amide compound-containing solution obtained upon producing a corresponding amide compound from a nitrile compound is processed with activated carbon.

DISCLOSURE OF THE INVENTION

The inventors have conducted earnest investigations with respect to a purification process of an amide compound-containing solution using activated carbon, and it has been found that when the amide compound-containing solution is made in contact with activated carbon under acidic conditions, and when it is made in contact with activated carbon in a region of a specific pH, impurities contained in the amide compound-containing solution, particularly proteins, can be extremely effectively removed.

It has been known according to the conventional knowledge that an amide compound having an unsaturated bond (for example, acrylamide, methacrylamide and the like, which are relatively important compounds in industry) are liable to cause polymerization reaction in an acidic region to make the compound unstable, and in order to avoid such phenomenon, it has been noted that it is important that the solution containing an amide compound is maintained neutral. The purification processing technique under the following conditions is unexpected from the conventional technique from these standpoints.

That is, the invention is (1) A purification process of an amide compound characterized by making an amide compound-containing solution in contact with activated carbon under acidic conditions;

(2) A purification process as described in the item (1), wherein the amide compound-containing solution is a product solution obtained by a hydration reaction of a corresponding nitrile compound;

(3) A purification process as described in the item (2), wherein the amide compound has from 2 to 20 carbon atoms;

(4) A purification process as described in the item (3), wherein the amide compound has an unsaturated bond;

(5) A purification process as described in the item (2) or (3), wherein the amide compound is produced by a hydration reaction of a nitrile compound by using a microorganism fungus body containing nitrile hydratase or a processed product of the microorganism fungus body;

(6) A purification process as described in the item (5), wherein the microorganism fungus body is a transformant obtained by expressing a nitrile hydratase gene cloned from the microorganism in an arbitrary host;

(7) A purification process as described in the item (4), wherein the amide compound is produced by a hydration reaction of a nitrile compound by using a microorganism fungus body containing nitrile hydratase or a processed product of the microorganism fungus body;

(8) A purification process as described in the item (7), wherein the microorganism fungus body is a transformant obtained by expressing a nitrile hydratase gene cloned from the microorganism in an arbitrary host;

(9) A purification process as described in the item (7), wherein the amide compound is acrylamide or methacrylamide;

(10) A purification process as described in the item (8), wherein the amide compound is acrylamide or methacrylamide;

(11) A purification process as described in the item (9) or (10), wherein the amide compound-containing solution has pH of from 3.5 to 6.5 upon contacting with the activated carbon;

(12) A purification process as described in the item (11), characterized in that the amide compound-containing solution is prepared to be acidic by using an organic acid having an acid dissociation exponent of from 3.5 to 5.5 or by using the organic acid and a base;

(13) A purification process as described in the item (12), wherein the organic acid is acrylic acid or methacrylic acid;

(14) A purification process as described in the item (13), wherein the activated carbon is activated carbon made from wood or palm shell as a raw material;

(15) A purification process as described in the item (14), wherein a temperature upon contact with the activated carbon is from 10° C. to 50° C.; and

(16) A purification process as described in the item (15), characterized in that after making the amide compound-containing solution in contact with the activated carbon, a liquid obtained by separating the activated carbon from the amide-containing solution is set at a saturation temperature or lower to deposit crystals.

BEST MODE FOR CARRYING OUT THE INVENTION

The amide compound-containing solution in the invention is not particularly limited, and specifically, an amide compound-containing solution obtained by hydrating a nitrile compound having from 2 to 20 carbon atoms is exemplified. The nitrile compound to be subjected to the hydration reaction includes a broad range of nitrile, for example, an aliphatic nitrile, an aromatic nitrile and the like. Examples of the aliphatic nitrile include a saturated or unsaturated nitrile having from 2 to 6 carbon atoms, for example, an aliphatic saturated mononitrile, such as aectonitrile, propionitrile, butylonitrile, isobutylonitrile, valeronitrile, isovaleronitrile, capronitrile and the like; an aliphatic saturated dinitrile, such as malononitrile, succinonitrile, adiponitrile and the like; and an aliphatic unsaturated nitrile, such as acrylonitrile, methacrylonitrile, crotononitrile and the like. Examples of the aromatic nitrile include benzonitrile, o-, m- and p-chlorobenzonitrile, o-, m- and p-fluorobenzonitrile, o-, m- and p-nitrobenzonitrile, o-, m- and p-toluenitrile, benzyl cyanide and the like. In particular, the purification process of the invention is preferred for an aqueous solution containing acrylamide or methacrylamide obtained by hydrating a nitrile compound having an unsaturated bond, such as acrylonitrile and methacrylonitrile.

The amide compound-containing solution to be processed in the invention may be those obtained by any known hydrating method. That is, it may be any of those obtained by a hydrating method by sulfuric acid, a contact hydrating method by a catalyst containing metallic copper, such as a Raney copper catalyst, a hydrating method by an enzyme having capability of hydrating a nitrile compound (nitrile hydratase), a microorganism fungus body containing the same, a processed product of the enzyme and the microorganism fungus body, and the like.

Among these, amide compound-containing solutions obtained by using nitrile hydratase, which is an enzyme having capability of hydrating a nitrile compound, a processed product of the nitrile hydratase, a microorganism fungus body containing the nitrile hydratase, a processed product of the microorganism fungus body, or the like are preferred for the purification process of the invention.

The nitrile hydratase referred herein is an enzyme having capability of hydrolyzing a nitrile compound to produce a corresponding amide compound.

The microorganism containing nitrile hydratase is not particularly limited as far as it produces nitrile hydratase having capability of hydrolyzing a nitrile compound to produce a corresponding amide compound, and it maintains an activity as nitrile hydratase in a 30% by weight aqueous solution of acrylamide. Specifically, preferred examples thereof include microorganisms belonging to *Nocardia, Corynebacterium, Bacillus, thermophilic Bacillus, Pseudomonas, Micrococcus, Rhodecoccus* represented by *rhodochrous, Acinetobacter, Xanthobacter, Streptomyces, Rhizobium, Klebsiella, Enterobacter, Erwinia, Aeromonas, Citrobacter, Achromobacter, Agrobacterium*, and *Pseudonocardia* represented by *thermophilia*.

A transformant obtained by expressing a nitrile hydratase gene cloned from the microorganism in an arbitrary host is also included in the microorganism of the invention. While *Escherichia coli* can be exemplified as described later as a representative example of the arbitrary host referred herein, it is not particularly limited to *Escherichia coli*, but Bacillus, such as *Bacillus subtilis* and the like, and other microorganism strains, such as yeast, actinomycete and the like are also included. Examples thereof include MT-10822 (the strain has been deposited in National Institute of Bioscience and Human Technology, Ministry of International Trade and Industry, 1-3, Higashi 1-chome, Tsukuba-shi, Ibaraki-ken, on Feb. 7, 1996 under Receipt No. FERM BP-5785 based on the Budapest Treaty and Regulations on the International Recognition of the Deposit of Microorganisms for the Purposes of Patent Procedure). The microorganism of the invention also includes a transformant obtained by expressing a mutant nitrile hydratase that has been further improved in amide compound resistance, nitrile compound resistance and temperature resistance by displacing, deleting, canceling or inserting one of or two or more of constitutional amino acids of the enzyme with other amino acids by using DNA splicing technique.

Upon producing an amide compound by using the foregoing microorganisms, a fungus body or a processed product of a fungus body is generally used. The fungus body can be prepared by utilizing an ordinary method having been known in the fields of molecular biology, bioengineering and genetic engineering. For example, such a method can be exemplified that after the microorganism is planted in an ordinary liquid culture medium, such as an LB medium, an M9 medium and the like, it is grown at an appropriate culture temperature (which is generally from 20° C. to 50° C., and 50° C. or higher is possible for thermophile), and then the microorganism is separated and recovered from the culture liquid by centrifugal separation.

The processed product of the microorganism fungus body in the invention denotes an extract and a trituration product of the microorganism fungus body, a post-separated product obtained by separating and purifying a nitrile hydratase active fraction of the extract and the trituration product, and a fixed product obtained by fixing the microorganism fungus body, or the extract, the trituration product or the post-separated product of the fungus body to an appropriate carrier, and these are included in the processed product of the fungus body of the invention as far as they has an activity as nitrile hydratase.

With respect to the amide compound to be purified in the invention, the mode of reaction when a nitrile compound is hydrated by using a microorganism fungus body containing nitrile hydratase or a processed product of the microorganism fungus body to obtain the amide compound may be a method where the corresponding nitrile compound is subjected to either a batch reaction or a continuous reaction. The mode of reaction is also not particularly limited and may be conducted, for example, with either a suspended bed or a fixed bed. The concentration of the catalyst, such as the fungus body of the microorganism or the processed product of the fungus body, in the reaction solution is not particularly limited as far as it does not impair admixture of an aqueous medium and the nitrile compound.

In the foregoing, the concentration of the nitrile compound in the case where the nitrile compound is added upon starting the reaction may be the saturated concentration of the nitrile compound. The upper limit of the concentration, on the other hand, is not particularly limited and can be arbitrarily determined depending on the assumed amide compound concentration and the assumed nitrile compound concentration upon completion of the reaction.

The unreacted nitrile compound can be removed from the reaction solution by such means as distillation or the like after the reaction. Therefore, it is possible that the nitrile compound is added in such a manner that the nitrile compound is still excessive even after the assumed amide compound concentration after completion of the reaction is obtained.

Specifically, in the case where the nitrile compound is acrylonitrile, the saturated concentration of the compound in water is about 7% by weight at 20° C., and thus it is preferably about 7% by weight or more. In the case where the nitrile compound is methacrylonitrile or crotononitrile, the saturated concentration of these compound in water is about 2% by weight at 20° C., and thus it is preferably about 2% by weight or more.

The foregoing amidation reaction is generally carried out under ordinary pressure, and it may be carried out under increased pressure in order to increase the solubility of the nitrile compound in the aqueous medium. The reaction temperature is not particularly limited as far as it is the freezing point of the aqueous medium or lower, and in the case where the catalyst contains nitrile hydratase, it is preferably carried out in the range of from 0° C. to 50° C., and more preferably from 10° C. to 30° C.

The pH of the reaction solution on the amidation reaction is not particularly limited as far as the activity of the nitrile hydratase is maintained, and it is preferably in the range of from pH 6 to 10, and more preferably in the range of from pH 7 to 9.

The purification of the amide compound in the invention is carried out by making the liquid containing the amide compound in contact with the activated carbon under acidic conditions, preferably pH 2 or more, and more preferably from pH 3.5 to 6.5.

While in order to make acidic the amide compound-containing solution in the invention, it is generally necessary that an acid is added to the amide compound-containing solution, wide ranges of species of acids can be used unless they adversely affect the stability of the amide compound, and examples thereof include a mineral acid, such as sulfuric acid, nitric acid and the like, an organic acid, such as acetic acid and acrylic acid, and the like, two or more kinds of which may be used. Among these, it is particularly preferred in the invention that the pH is adjusted to the foregoing range by using both a weak acid and a base because the adjustment of pH can be more conveniently and stably carried out, the use of a weak acid is effective for obtaining high purifying efficiency and the stability of the amide compound, and the pH buffering effect can be obtained.

A weak acid that can be preferably used preferably has an acid dissociation exponent (pKa, at 25° C. in water) of from 2.0 to 6.0, and more preferably from 3.5 to 5.5. Representative example of the acid include an aliphatic saturated monocarboxylic acid, such as acetic acid, propionic acid, octanoic acid, valeric acid and the like, an aliphatic unsaturated monocarboxylic acid, such as acrylic acid, crotonic acid, methacrylic acid and the like, and an aliphatic polycarboxylic acid, such as oxalic acid, adipic acid, succinic acid, maleic acid and the like, and an aromatic carboxylic acid such as benzoic acid and the like. A strong base is preferred as the base, and examples thereof include sodium hydroxide, potassium hydroxide and the like.

In the case where the amide compound to be processed in the invention has an unsaturated bond, problems are caused upon subjecting it after purification to a polymerization reaction when the acid remains, or is released in the resulting polymer. Therefore, in the case where the amide compound having an unsaturated bond is to be purified, an acid having an unsaturated bond and being capable of suffering copolymerization with the amide compound, specifically acrylic acid, methacrylic acid, crotonic acid and the like, is preferably used.

The concentration of the acid or the concentrations of the acid and the base in the invention is generally in the range of from 10 ppm by weight to 5% by weight in terms of the acid based on the amide compound-containing solution while it depends on the nature of the amide compound-containing solution and the pKa of the acid to be used.

In the invention, while the amide compound-containing solution is made in contact with the activated carbon under acidic conditions, there is no particular limitation as long as the amide compound-containing solution is acidic or has a form to be acidic upon contacting with the activated carbon, and such a method may be employed without problem that the amide compound-containing solution is prepared under acidic condition simultaneously with the addition of the activated carbon.

The activated carbon used in the invention is not particularly limited, and powdery ones and granular ones can be used. As for the apparatus for carrying out the purification process, those suitable for the particle size of the activated carbon can be used. For example, in the case where powdery activated carbon is used, the process can be carried out by either a batch system or a continuous system in a vessel capable of carrying out agitation of the solution. In the case where granular activated carbon is used, a continuous processing using a packed tower system can be used in addition to the foregoing systems.

While activated carbon generally includes those using coal, wood, palm shell and the like as a raw material, there is no particular limitation as long as it has adsorption power, and any kind of them can be used.

However, in the case where the amide compound to be processed has an unsaturated bond, it is preferred to use activated carbon having a small metal content taking the storage stability and the easiness of polymerization of the amide compound into consideration, and it is more preferred to use those obtained from wood or palm shell as a raw material.

With respect to the amount of the activated carbon used upon carrying out the purification process in the invention, sufficient purification effect cannot be obtained when it is too small, whereas it is uneconomical when it is too large, and therefore, the using amount thereof is generally from 0.01 to 20% by weight, and more preferably from 0.05 to 10% by weight, based on the amide compound-containing solution.

In the particular case where powdery activated carbon is used, the activated carbon as it is may be directly added to the amide compound-containing solution, or in alternative, it is possible that the activated carbon is once dispersed in a medium, such as water or the like, to make a slurry, which is then added or supplied to the amide compound-containing solution.

The temperature when the amide compound-containing solution is subjected to the purification process by activated carbon in the invention is not particularly limited as far as the amide compound is not deposited as crystals, and the stability thereof is not affected, and it is generally carried out in the range of from 0° C. to 80° C. Particularly, in the case where a solution containing an amide compound having an unsaturated bond, such as acrylamide and methacrylamide, is subjected to the purification process, it is preferably made in contact with the activated carbon at 60° C. or lower, and more preferably in the range of from 10° C. to 50° C., in order to prevent gelation caused by occurrence of a polymerization reaction. The period of time required for the contact process with the activated carbon is generally in the range of from 0.5 to 20 hours while it depends on the mode of processing and the amount of the activated carbon.

Subsequently, the activated carbon is separated from the amide compound-containing solution having been subjected to the contact process, so as to obtain a purified solution of the amide compound-containing solution. The method for separating the activated carbon is not particularly limited as far as it is a method using a solid-liquid separating apparatus that is generally used, example of which include a pressure filtering apparatus, a vacuum filtering apparatus, a centrifugal separator and the like, and further, it may be either a batch system or a continuous system.

It is also possible in the invention that a further purified amide compound is obtained in such a manner that the amide compound-containing solution having been separated from the activated carbon is cooled to crystallize the objective amide compound from the solution.

In the example, the acquisition of an amino acid substituted body maintaining the nitrile hydratase activity is carried out by site-specific mutation. However, the similar results as the example can be obtained by such a manner that a spliced plasmid is obtained by other methods than the site-specific mutation based on the mutation point and the species of the substituted bases disclosed in the example, and is then introduced into the host cell.

For example, a DNA fragment having such a base sequence that the base sequence of the DNA in the region corresponding to the mutation point disclosed in the example is the sequence after substitution of amino acids is synthesized by a DNA synthesizer or the like, and the resulting fragment and the region of the pPT-DB1 having been separated corresponding to the fragment are substituted by each other, whereby the objective spliced plasmid can be obtained.

EXAMPLES

The invention will be described in more detail below with reference to the examples, but the invention is not construed as being limited to the examples.

In the following, HPLC analysis of a reaction solution is carried out by using ULTRON 80HG (50 mm×8 mm in diameter) as a column and a 10 mM phosphoric acid aqueous solution as a developer, and acrylamide is detected by optical absorbance at 220 nm. In order to confirm the effect of the invention, proteins contained in the resulting amide compound-containing solution are analyzed. The protein concentration is determined by using a protein analysis kit produced by Biorat Laboratories, Inc. after the amide compound contained in the amide compound-containing solution is removed by dialysis using a semipermeable membrane, whereby the removal rate of proteins.

Example 1

100 ml of a culture medium of the following composition was prepared in a 500-ml Erlenmeyer flask with a baffle and was sterilized in an autoclave at 121° C. for 20 minutes. After adding ampicillin to the culture medium to make a final concentration of 50 μg/ml, one platinum loop of the MT-10822 strain (FERM BP-5785) was planted and cultured at 37° C. and 130 rpm for 20 hours. Only the fungus body was separated from the culture liquid by centrifugal separation (15,000 G for 15 minutes), and after again suspending the fungus body in 50 ml of physiological saline, a wet fungus body is obtained by again conducting centrifugal separation.

| Culture Medium Composition | |
|---|---|
| Yeast extract | 5.0 g/L |
| Polypepton | 10.0 g/L |
| NaCl | 5.0 g/L |
| Cobalt chloride hexahydrate | 10.0 mg/L |
| Ferric sulfate heptahydrate | 40.0 mg/L |
| pH 7.5 | |

1.5 g of the wet fungus body obtained in the foregoing was suspended in 98.5 g of 0.3 mM-NaOH aqueous solution, and 36 g of acrylonitrile was added to the suspension at once, followed by carrying out the reaction under agitation at 10° C. After 24 hours from the start of the reaction, the reaction solution was analyzed by the HPLC analysis. As a result, only acrylamide (concentration: 35% by weight) was present in the reaction solution but no acrylonitrile was confirmed. The pH of the reaction solution was 8.0.

The reaction solution was adjusted to pH 5 by a 10% sulfuric acid aqueous solution, to which 2% by weight based on the reaction solution of activated carbon (powdery activated carbon PM-SX produced by Mitsukura Chemical Co., Ltd.) was added, and after agitating at 25° C. for 5 hours, filtration was carried out by using filter paper. The protein concentration of the resulting filtrate was measured, and the removing rate was 99% or more. No white turbidity was caused when 100 ml of methanol was added to 10 ml of the filtrate, and no polymer was observed.

Example 2

A filtrate was obtained in the same manner as Example 1 except that the reaction solution obtained in Example 1 was adjusted to pH 5 by a 10% acrylic acid aqueous solution. The protein concentration of the filtrate was measured, and the removing rate was 99% or more. No white turbidity was caused when 100 ml of methanol was added to 10 ml of the filtrate, and no polymer was observed.

Example 3

Acquisition of Amino Acid Substituted Body Maintaining Nitrile Hydratase Activity In order to substitute the sixth Leu on the α subunit by Met, the site-specific mutational introduction was carried out by using "LA PCR in vittro mutagenesis Kit" produced by Takara Shuzo Co., Ltd. using the pPT-DB1 plasmid DNA obtained according to JP-A-9-275978 as a template. Hereinafter, the "LA PCR in vittro mutagenesis Kit" will be simply referred to as a kit. The following examples basically followed the principal and the operation procedure of the kit.

10 ml of an LB liquid culture medium was prepared in a 30-ml test tube and was sterilized in an autoclave at 121° C. for 20 minutes. After adding ampicillin to the culture medium to make a final concentration of 100 μg/ml, one platinum loop of the MT-10822 strain was planted and cultured at 37° C. and 300 rpm for 20 hours. After fractionating 1 ml of the culture liquid to a suitable centrifugal tube, the fungus body was separated by centrifugal separation (15,000 rpm for 5 minutes). Subsequently, the plasmid DNA of pPT-DB1 was prepared from the fungus body by the alkali SDS extraction method.

Two kinds of PCR reactions were carried out by using 1 μg of the plasmid DNA of pPT-DB1 as a template. The PCR reaction No. 1 was carried out by repeating a procedure of 15 seconds of thermal denaturation (98° C.), 30 seconds of annealing (55° C.) and 120 seconds of elongation reaction (72° C.) by 25 cycles in a system of a total amount of 50 μl containing 50 pmol each of the primer described in the sequence number 1 of the sequence table and the M13 primer M4 (arrangement disclosed in the sequence number 2 in the sequence table) (the composition was in accordance with the conditions described in the kit). The PCR reaction No. 2 was carried out by conducting the same procedure as in the PCR reaction No. 1 in a system of a total amount of 50 μl containing 50 pmol each of the MUT4 primer (arrangement disclosed in the sequence number 3 in the sequence table) and the M13 primer RV (arrangement disclosed in the sequence number 4 in the sequence table). Analysis of DNA amplified products was carried out for 5 μl each of the reaction completed solutions of the PCR reactions No. 1 and No. 2 by agarose electrophoresis (agarose concentration: 1.0% by weight), and the presence of the DNA amplified product was confirmed. The excessive primers and the dNTP were removed from the respective PCR reaction completed solution by using Microcon 100 (produced by Takara Shuzo Co., Ltd.), and then TE was added thereto to prepare 50 μl each of the solutions. Annealing solutions of a total amount of 47.5 μl containing 0.5 μl each of the TE solutions (the composition was in accordance with the conditions described in the kit) were prepared, and after carrying out a thermal denaturation treatment (98° C.) for 10 minutes, cooling was carried at to 37° C. over 60 minutes at a constant rate, followed by maintaining at 37° C. for 15 minutes, so as to conduct the annealing treatment. 0.5 μl of TAKARALA Taq was added to the annealing treatment solution, which was subjected to a heat treatment at 72° C. for 3 minutes, so as to complete a heterodouble strand. 50 pmol each of the M13 primer M4 (arrangement disclosed in the sequence number 2 in the sequence table) and the M13 primer RV (arrangement disclosed in the sequence number 4 in the sequence table) were added to make a total amount of 50 μl, and then the PCR reaction No. 3 was carried out by repeating a procedure of 15 seconds of thermal denaturation (98° C.), 30 seconds of annealing (55° C.) and 120 seconds of elongation reaction (72° C.) by 25 cycles. Analysis of DNA amplified products was carried out for 5 μl of the reaction completed solutions of the PCR reaction No. 3 by agarose electrophoresis (using low melting point agarose Type VII produced by Sigma Aldrich Japan, Inc., agarose concentration: 0.8 by weight), and the presence of about 2.0 Kbp of the DNA amplified product was confirmed. Subsequently, only a DNA fragment of about 2.0 kbp was cut out from the agarose gel, and after finely pulverizing the agarose fragment (about 0.1 g), which was suspended in 1 ml of the TE solution, it was kept at 55° C. for 1 hour to completely melt the agarose. Phenol/chloroform extraction and ethanol precipitation were carried out for the molten solution in ordinary procedures to purify the DNA fragment, and it was finally dissolved in 10 μl of TE. After cutting about 2.0 kbp of the purified DNA fragment by the restriction enzymes EcoRI and HindIII, phenol/chloroform extraction and ethanol precipitation were carried out for the restriction enzyme treated solution to purify the DNA fragment, and it was finally dissolved in 10 μl of TE. Similarly, the pPT-DB1 was cut by EcoRI and HindIII as the sole restriction enzyme site on the pPT-DB1, and agarose electrophoresis was carried out (using low melting point agarose Type VII produced by Sigma Aldrich Japan, Inc., agarose concentration: 0.7 by weight), so as to cut out only about 2.7 Kbp of the DNA fragment from the agarose gel. After the agarose fragment (about 0.1 g) thus cut out was finely pulverized and suspended in the TE solution, it was maintained at 55° C. for 1 hour to completely melt the agarose. Phenol/chloroform extraction and ethanol precipitation were carried out for the molten solution in ordinary procedures to purify the DNA fragment, and it was finally dissolved in 10 μl of TE. The amplified DNA product thus obtained and the pPT-DB1 fragment were ligated by using a DNA ligation kit (produced by Takara Shuzo Co., Ltd.), and then competent cells of *Escherichia coli* HB101 (produced by Toyobo Co., Ltd.) was transformed to prepare an *Escherichia coli* bank.

10 mL of an LB culture medium containing 40 μg/ml of ferric sulfate heptahydrate and 10 μg/ml of cobalt chloride dihydrate (hereinafter, referred to as an activity expression culture medium) was prepared in a 30-ml test tube and sterilized by an autoclave at 121° C. for 20 minutes. After adding ampicillin to the culture medium to make a final concentration of 100 μg/ml, one platinum loop each of five clones arbitrarily selected from the *Escherichia coli* bank was planted and cultured at 37° C. and 300 rpm for 20 hours. After fractionating 1 ml of the culture liquid to a suitable centrifugal tube, the fungus body was separated by centrifugal separation (15,000 rpm for 5 minutes). The fungus body was suspended in 200 μl of a potassium phosphate buffer solution (pH 7.0), and 1% by weight of acrylonitrile was added thereto, followed by reacting at 10° C. for 2 minutes. The same amount as the reaction solution of a 1-M phosphoric acid aqueous solution was added to the reaction solution to terminate the reaction, and the concentration of acrylamide thus produced was measured by the similar HPLC analysis as Example 2 As a result, production of acrylamide was confirmed in four clones among the five clones, and thus it was confirmed that the nitrile hydratase was maintained.

Fungus bodies of the four clones were separated from 1 ml each of the reminders of the culture medium having been subjected to the measurement of the nitrile hydratase activity, plasmid DNA of the respective clones was prepared by the alkali SDS extraction method. Subsequently, the base sequences of the nitrile hydratase structural genes of the respective clones were determined by the primer extension method using a sequencing king and Autosequencer 373A produced by ABI Inc. As a result, in the clone No. 1 shown in Table 1, the sixth Leu on the α subunit of the nitrile hydratase was substituted by Met.

TABLE 1

| Clone NO. | Mutation point (in α subunit) | Change of amino acid sequence | | Change of base sequence | |
|---|---|---|---|---|---|
| | | Before substitution | After substitution | Before substitution | After substitution |
| No. 1 | α-sixth | Leu | Met | CTG | ATG |

Subsequently, in order to substitute the 126th Phe on the α subunit by Tyr, a site-specific mutational introduction was carried out by using the plasmid DNA of the clone No. 1 as a template in the same procedures as in the foregoing.

in the case of the clone No. 1. As a result, in the clone No. 2 shown in Table 2, the sixth Leu on the α subunit of the nitrile hydratase was substituted by Met, and the 126th Phe on the α subunit was substituted by Tyr.

TABLE 2

| Clone NO. | Mutation point (in α subunit) | Change of amino acid sequence | | Change of base sequence | |
| --- | --- | --- | --- | --- | --- |
| | | Before substitution | After substitution | Before substitution | After substitution |
| No. 2 | α-sixth | Leu | Met | CTG | ATG |
| | α-126th | Phe | Tyr | TTC | TAC |

That is, 10 ml of an LB liquid culture medium was prepared in a 30-ml test tube and was sterilized in an autoclave at 121° C. for 20 minutes. After adding ampicillin to the culture medium to make a final concentration of 100 μg/ml, one platinum loop of the clone No. 1 strain was planted and cultured at 37° C. and 300 rpm for 20 hours. After fractionating 1 ml of the culture liquid to a suitable centrifugal tube, the fungus body was separated by centrifugal separation (15,000 rpm for 5 minutes) Subsequently, the plasmid DNA of the clone No. 1 was prepared from the fungus body by the alkali SDS extraction method.

Two kinds of PCR reactions were carried out by using 1 μg of the plasmid DNA of the clone No. 1 strain as a template. The PCR reaction No. 4 was carried out by repeating a procedure of 15 seconds of thermal denaturation (98° C.), 30 seconds of annealing (55° C.) and 120 seconds of elongation reaction (72° C.) by 25 cycles in a system of a total amount of 50 μl containing 50 pmol each of the primer described in the sequence number 5 of the sequence table and the M13 primer M4 (arrangement disclosed in the sequence number 2 in the sequence table) (the composition was in accordance with the conditions described in the kit). The PCR reaction No. 5 was carried out by conducting the same procedure as in the PCR reaction No. 4 in a system of a total amount of 50 μl containing 50 pmol each of the MUT4 primer (arrangement disclosed in the sequence number 3 in the sequence table) and the M13 primer RV (arrangement disclosed in the sequence number 4 in the sequence table). Analysis of DNA amplified products was carried out for 5 μl each of the reaction completed solutions of the PCR reactions No. 4 and No. 5 by agarose electrophoresis (agarose concentration: 1.0% by weight), and the presence of the DNA amplified product was confirmed. An *Escherichia coli* bank was prepared in the same manner as in the case of the clone No. 1.

One platinum loop each of five clones arbitrarily selected from the *Escherichia coli* bank was planted in the same activation expression culture medium as in the case of the clone No. 1 and cultured at 37° C. and 300 rpm for 20 hours. After fractionating 1 ml of the culture liquid to a suitable centrifugal tube, the nitrile hydratase activity was measured. As a result, production of acrylamide was confirmed in four clones among the five clones, and thus it was confirmed that the nitrile hydratase was maintained.

Fungus bodies of the four clones were separated from 1 ml each of the reminders of the culture medium having been subjected to the measurement of the nitrile hydratase activity, plasmid DNA of the respective clones was prepared by the alkali SDS extraction method. Subsequently, the base sequences of the nitrile hydratase structural genes of the respective clones were determined by the same procedures as Subsequently, in order to substitute the 212th Ser on the β subunit by Tyr, a site-specific mutational introduction was carried out by using the plasmid DNA of the clone No. 2 as a template in the same procedures as in the foregoing.

That is, 10 ml of an LB liquid culture medium was prepared in a 30-ml test tube and was sterilized in an autoclave at 121° C. for 20 minutes. After adding ampicillin to the culture medium to make a final concentration of 100 μg/ml, one platinum loop of the clone No. 2 strain was planted and cultured at 37° C. and 300 rpm for 20 hours. After fractionating 1 ml of the culture liquid to a suitable centrifugal tube, the fungus body was separated by centrifugal separation (15,000 rpm for 5 minutes). Subsequently, the plasmid DNA of the clone No. 1 was prepared from the fungus body by the alkali SDS extraction method.

Two kinds of PCR reactions were carried out by using 1 μg of the plasmid DNA of the clone No. 2 strain as a template. The PCR reaction No. 6 was carried out by repeating a procedure of 15 seconds of thermal denaturation (98° C.), 30 seconds of annealing (55° C.) and 120 seconds of elongation reaction (72° C.) by 25 cycles in a system of a total amount of 50 μl containing 50 pmol each of the primer described in the sequence number 6 of the sequence table and the M13 primer M4 (arrangement disclosed in the sequence number 2 in the sequence table) (the composition was in accordance with the conditions described in the kit). The PCR reaction No. 7 was carried out by conducting the same procedure as in the PCR reaction No. 6 in a system of a total amount of 50 μl containing 50 pmol each of the MUT4 primer (arrangement disclosed in the sequence number 3 in the sequence table) and the M13 primer RV (arrangement disclosed in the sequence number 4 in the sequence table). Analysis of DNA amplified products was carried out for 5 μl each of the reaction completed solutions of the PCR reactions No. 6 and No. 7 by agarose electrophoresis (agarose concentration: 1.0% by weight), and the presence of the DNA amplified product was confirmed. An *Escherichia coli* bank was prepared in the same manner as in the case of the clone No. 1.

One platinum loop each of five clones arbitrarily selected from the *Escherichia coli* bank was planted in the same activation expression culture medium as in the case of the clone No. 1 and cultured at 37° C. and 300 rpm for 20 hours. After fractionating 1 ml of the culture liquid to a suitable centrifugal tube, the nitrile hydratase activity was measured. As a result, production of acrylamide was confirmed in four clones among the five clones, and thus it was confirmed that the nitrile hydratase was maintained.

Fungus bodies of the four clones were separated from 1 ml each of the reminders of the culture medium having been subjected to the measurement of the nitrile hydratase activity, plasmid DNA of the respective clones was prepared by the alkali SDS extraction method. Subsequently, the base sequences of the nitrile hydratase structural genes of the respective clones were determined by the same procedures as in the case of the clone No. 1. As a result, in the clone No. 3 shown in Table 3, the 212th Ser on the β subunit was substituted by Tyr.

TABLE 3

| Clone NO. | Mutation point | Change of amino acid sequence | | Change of base sequence | |
|---|---|---|---|---|---|
| | | Before substitution | After substitution | Before substitution | After substitution |
| No. 3 | α-sixth | Leu | Met | CTG | ATG |
| | α-126th | Phe | Tyr | TTC | TAC |
| | β-212th | Ser | Tyr | TCC | TAC |

The fungus body of the clone No. 3 was cultured in the same manner as in Example 1 to obtain a fungus body required for the reaction.

Furthermore, 1.5 g of the wet fungus body thus obtained was suspended in 98.5 g of 0.3 mM-NaOH aqueous solution, and 60 g of acrylonitrile was added to the suspension at once, followed by carrying out the reaction under agitation at 10° C. After 24 hours from the start of the reaction, the reaction solution was analyzed by the HPLC analysis. As a result, only acrylamide (concentration: 50% by weight) was present in the reaction solution but no acrylonitrile was confirmed. The pH of the reaction solution was 8.0.

The reaction solution was adjusted to pH 5 by a 10% sulfuric acid aqueous solution, to which 2% by weight based on the reaction solution of activated carbon (powdery activated carbon PM-SX produced by Mitsukura Chemical Co., Ltd.) was added, and after agitating at 25° C. for 5 hours, filtration was carried out by using filter paper. The removing rate of protein of the resulting filtrate was measured, and the removing rate was 99% or more. No white turbidity was caused when 100 ml of methanol was added to 10 ml of the filtrate, and no polymer was observed.

Example 4

The same procedures as in Example 1 were carried out except that the hydration reaction solution obtained in Example 3 was adjusted to pH 3 by a 10% sulfuric acid aqueous solution, so as to obtain a filtrate. The removing rate of protein of the resulting filtrate was measured, and the removing rate was 75%. No white turbidity was caused when 100 ml of methanol was added to 10 ml of the filtrate, and no polymer was observed.

Comparative Example 1

The same procedures as in Example 1 were carried out except that the hydration reaction solution obtained in Example 3 was adjusted to pH 7 by a 10% sulfuric acid aqueous solution, so as to obtain a filtrate. The removing rate of protein of the resulting filtrate was measured, and the removing rate was 25%.

ADVANTAGE OF THE INVENTION

As is clear from the foregoing description and the results of the Examples and the Comparative Examples, according to the process of the invention, purification of an amide compound can be carried out by contacting with activated carbon under acidic conditions with far higher efficiency in comparison to the conventional purification process by activated carbon. In particular, when acrylamide purified by the process of the invention is polymerized, such polyacrylamide is obtained that has a high molecular weight, is excellent in storage stability, and has high solubility in water.

---

The invention claimed is:

1. A process for purifying an amide compound, comprising contacting an amide compound-containing solution with activated carbon under acidic conditions of from pH of 3.5 to 6.5, and
separating the activated carbon from the amide compound-containing solution, thereby removing proteins from the amide compound-containing solution, wherein;
the amide compound has an unsaturated bond and is produced by contacting a nitrile compound with a nitrile hydratase, a microorganism comprising a nitrile hydratase, or a processed product of the microorganism, wherein the processed product comprises nitrile hydratase.

2. A purification process according to claim 1, wherein the amide compound has from 2 to 20 carbon atoms.

3. A purification process according to claim 2, wherein the amide compound is aciylamide or methacrylamide.

4. A purification process according to claim 1, wherein the amide compound-containing solution is prepared to be acidic by using an organic acid having an acid dissociation exponent of from 3.5 to 5.5 or by using said organic acid and a base.

5. A purification process according to claim 4, wherein the organic acid is acrylic acid or methaciylic acid.

6. A purification process according to claim 5, wherein the activated carbon is activated carbon made from wood or palm shell as a raw material.

7. A purification process according to claim 6, wherein a temperature upon contact with said activated carbon is from 10 to 50° C.

8. A purification process according to claim 7, wherein after separating said activated carbon from said amide-containing solution, said amide-containing solution is set at a saturation temperature or lower to deposit crystals.

9. The purification process according to claim 1, wherein the amide compound has from 2 to 20 carbon atoms.

10. A purification process according to claim 1, wherein the amide compound-containing solution has pH of from 3.5 to 6.5 upon contacting with the activated carbon.

11. A purification process according to claim 10, wherein the amide compound-containing solution is prepared to be acidic by using an organic acid having an acid dissociation exponent of from 3.5 to 5.5 or by using said organic acid and a base.

12. A purification process according to claim 11, wherein the organic acid is acrylic acid or methacrylic acid.

13. A purification process according to claim 12, wherein the activated carbon is activated carbon made from wood or palm shell as a raw material.

14. A purification process according to claim 13, wherein a temperature upon contact with said activated carbon is from 10 to 50° C.

15. A purification process according to claim 14, wherein after separating said activated carbon from said amide-containing solution, the amide compound-containing solution is set at a saturation temperature or lower to deposit crystals.

* * * * *

UNITED STATES PATENT AND TRADEMARK OFFICE
CERTIFICATE OF CORRECTION

PATENT NO. : 7,700,330 B2
APPLICATION NO. : 09/936514
DATED : April 20, 2010
INVENTOR(S) : Takeya Abe et al.

It is certified that error appears in the above-identified patent and that said Letters Patent is hereby corrected as shown below:

On the Title page, under (86) PCT No., change:

"PCT/JP01/00313" to --PCT/JP01/00131--.

Signed and Sealed this

Twenty-third Day of November, 2010

David J. Kappos
*Director of the United States Patent and Trademark Office*